United States Patent [19]
Isoyama et al.

[11] Patent Number: 5,300,017
[45] Date of Patent: Apr. 5, 1994

[54] APPARATUS FOR DRIVING INTRA-AORTA BALLOON PUMP

[75] Inventors: Takashi Isoyama, Tokyo; Sadahiko Mushika, Ichinomiya, both of Japan

[73] Assignee: Aisin Seiki Kabushiki Kaisha, Kariya, Japan

[21] Appl. No.: 889,976

[22] Filed: May 29, 1992

[30] Foreign Application Priority Data

May 29, 1991 [JP] Japan .................. 3-155273

[51] Int. Cl.$^5$ .............................. A61M 1/10
[52] U.S. Cl. ...................................... 600/18
[58] Field of Search ........................ 604/4–6; 600/18; 623/3

[56] References Cited

U.S. PATENT DOCUMENTS

| | | | |
|---|---|---|---|
| 4,796,606 | 1/1989 | Mushika . | |
| 4,974,774 | 12/1990 | Nakagawa et al. | 623/3 |
| 5,169,379 | 12/1992 | Freed et al. | 600/18 |

Primary Examiner—Lee S. Cohen
Assistant Examiner—Marianne Parker
Attorney, Agent, or Firm—Burns, Doane, Swecker & Mathis

[57] ABSTRACT

An apparatus for driving an intra-aorta balloon pump is comprised of an isolator having a housing in which a first chamber and a second chamber are defined by a membrane, a positive pressure source which is in fluid communication with the first chamber via a first timing valve, a negative pressure source which is in fluid communication with the first chamber via a second timing valve, a space defined between the second chamber and the intra-aorta balloon pump and containing an amount of operating fluid, a tank for storing therein the operating fluid, an inlet valve interposed between the tank and the space, an exhaust valve interposed between the space and the atmospheric pressure, a sensor for measuring the pressure in the space, and a controller to be operated in such a manner that the first timing valve and the second timing valve are opened and closed alternately in order to establish an alternate supply of the positive and negative pressures to the first chamber and each time-duration during which the first timing valve is opened is set to be decreased gradually with the passing of time.

4 Claims, 3 Drawing Sheets

Fig. 3
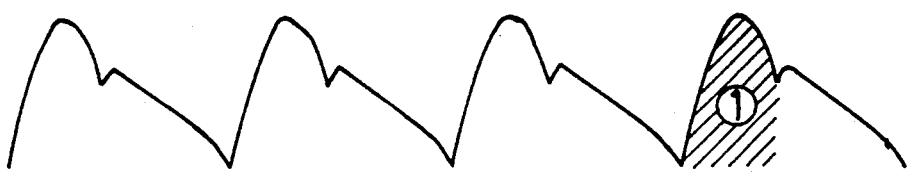
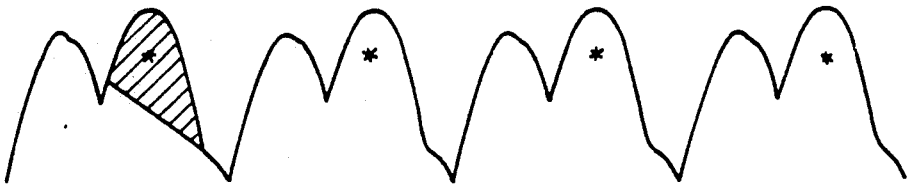
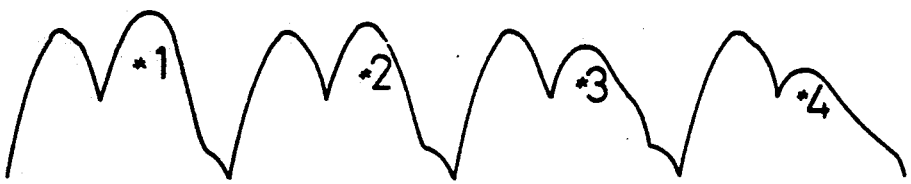

APPARATUS FOR DRIVING INTRA-AORTA BALLOON PUMP

BACKGROUND OF THE INVENTION

The present invention relates to an apparatus for driving an intra-aorta balloon pump which is designed to expand and contract the intra-aorta balloon pump by alternately supplying positive and negative pressures thereto.

In general, it is preferable that the volume of the expansion of an intra-aorta balloon pump should be changed in accordance with the degree of recovery of the living heart. In order to meet with this requirement, an improved device has been provided which is shown in U.S. Pat. No. 4,796,606 for example. In this device, the expansion of intra-aorta balloon pump can be changed on the basis of a difference between the pressure in the balloon pump and the blood pressure of the patient.

However, in this conventional device, once the expansion of the intra-aorta balloon pump has been changed, the resulting expansion can't be changed furthermore so long as the device is in operation. In other words, while the device is running, the pressure change in or the expansion degree of the intra-aorta balloon pump is constant. Thus, it is difficult to establish a precise change of the expansion degree of the intra-aorta balloon pump in accordance with the recovery of the patient.

SUMMARY OF THE INVENTION

It is, therefore, a primary object of the present invention to provide an apparatus for driving an intra-aorta balloon pump without the foregoing drawback.

It is another object of the present invention to provide an apparatus for driving an intra-aorta balloon pump in which a precise change of the expansion degree thereof can be established in accordance with the recovery of the patient.

In order to attain the foregoing objects, an apparatus for driving an intra-aorta balloon pump is comprised of an isolator having a housing in which a first chamber and a second chamber are defined by a membrane, a positive pressure source which is in fluid communication with the first chamber via a first timing valve, a negative pressure source which is in fluid communication with the first chamber via a second timing valve, a space defined between the second chamber and the intra-aorta balloon pump and containing an amount of operating fluid, a tank for storing therein the operating fluid, an inlet valve interposed between the tank and the space, an exhaust valve interposed between the space and the atmospheric pressure, a sensor for measuring the pressure in the space, and a controller to be operated in such a manner that the first timing valve and the second timing valve are opened and closed alternately in order to establish an alternate supply of the positive and negative pressures to the first chamber and each time-duration during which the first timing valve is opened is set to be decreased gradually with the passing of time.

BRIEF DESCRIPTION OF THE DRAWINGS

The above and other objects, features and advantages of the present invention will be more apparent and more readily appreciated from the following detailed description of preferred exemplarily embodiment of the present invention, taken in connection with the accompanying drawings, in which;

FIG. 3 is a view showing the result derived from the present invention in comparison with the conventional example.

DESCRIPTION OF THE PREFERRED EMBODIMENT

One embodiment of the present invention will be described hereinunder in detail with reference to the accompanying drawings.

Figure 1:
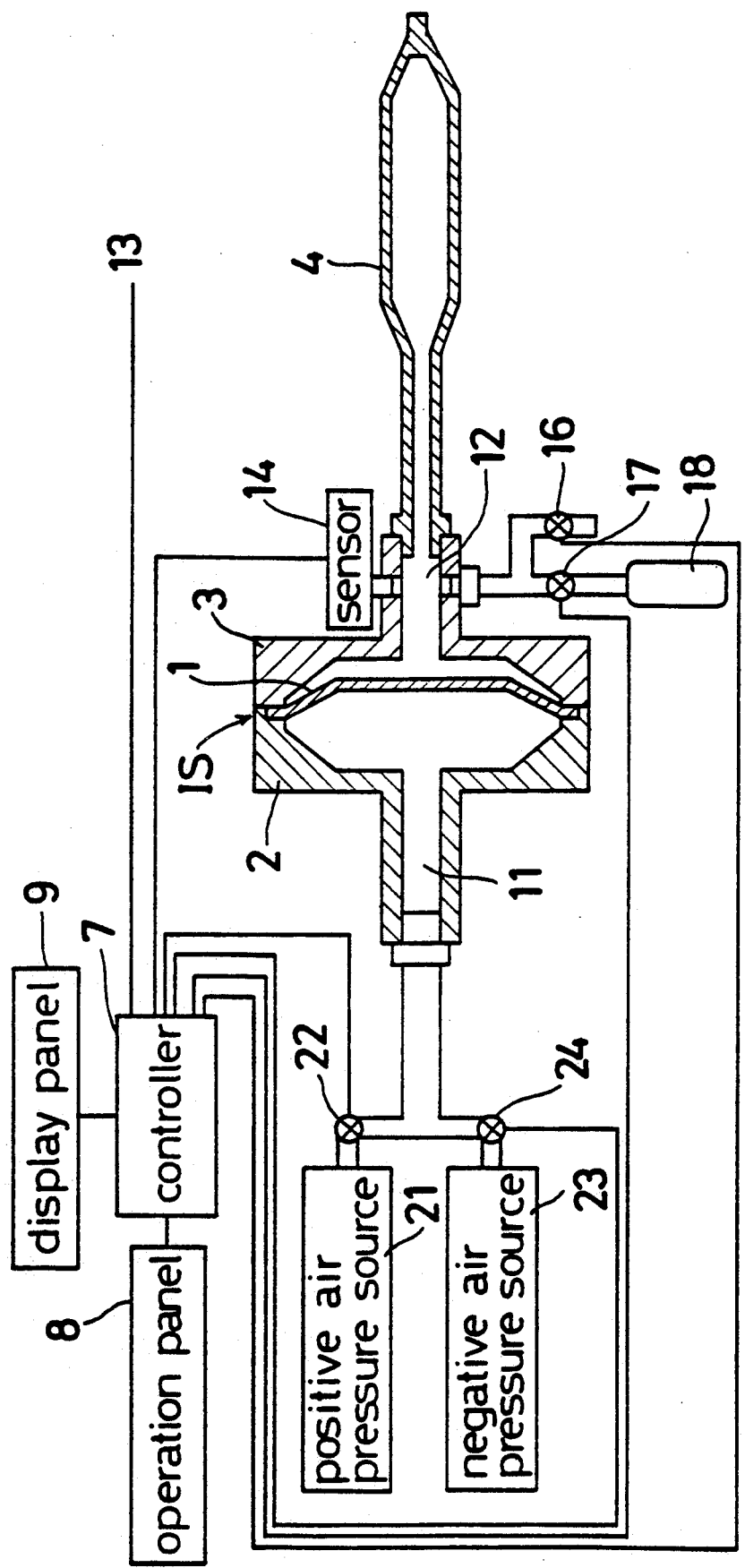
FIG. 1 is a block diagram of one embodiment of an apparatus for driving an intra-aorta balloon pump according to the present invention.

Referring to FIG. 1, which is a block diagram of a pumping device for operating an intra-aortic balloon pump in accordance with the present invention, the device has an isolator IS. A housing of the isolator IS which is established or constituted by a first sector 2 and a second sector 3 is provided therein with an inner space which is divided by a membrane 1 made of a flexible material such as rubber into a first chamber 11 and a second chamber 12. The membrane 1 in the form of the diaphragm is clamped between the sectors 1 and 2.

The first chamber 11 is in fluid communication, via a first timing valve 22 and a second timing valve 24, with a first compressor 21 which serves as a positive air pressure source and a second compressor 21 which serves as a negative air pressure source 23, respectively.

The second chamber 12 is in fluid communication with an intra-aortic balloon pump 4 which is to be inserted or introduced into a human aorta (not shown) via his/her femora artery. An inner space or an interior space defined between the second chamber 12 which is a closed one filled with a proper amount of helium. The second chamber 12 is in fluid communication, via an inlet valve 17 and an exhaust valve 16, with a tank 18 for storing therein an amount of helium and the atmosphere, respectively. The pressure in the second chamber 12 is set to be measured by a sensor 14.

In the foregoing pumping device, while the first timing valve 22 is being opened (closed) and the second timing valve 24 is being closed (opened), the membrane 1 is set to be deformed in the rightward (leftward) direction, thereby to expand (contract) the balloon pump 4. Thus, the isolator IS changes a medium for driving the balloon pump 4 from air to helium, which results in that the driving medium being made safe for living organisms. When the membrane is in engagement with the first sector 2 during extraction of the balloon pump 4, the amount of helium at this time is defined as the foregoing proper amount of helium. The opening time t (unit:msec) while the first timing valve 22 is being opened is adjusted in order that when the balloon pump 4 is expanded the pressure in the second chamber 12 may be slightly greater than the maximum blood pressure of the patient. In this embodiment, such pressure in the second chamber 12 is set to be 10 mmHg.

In order to control the first timing valve 22, the second timing valve 24, the inlet valve 17, and the exhaust valve 16, a controller 7 which is in the form of the micro-processor is provided an output of the sensor 14 and a blood pressure 13 of the patient are inputted to the microprocessor. An operation panel 8 is used for the setting-up of the controller 7, and a display panel 9 is used for displaying information relating to the living organization of the patient and the driving of the balloon pump 4.

Figure 2:
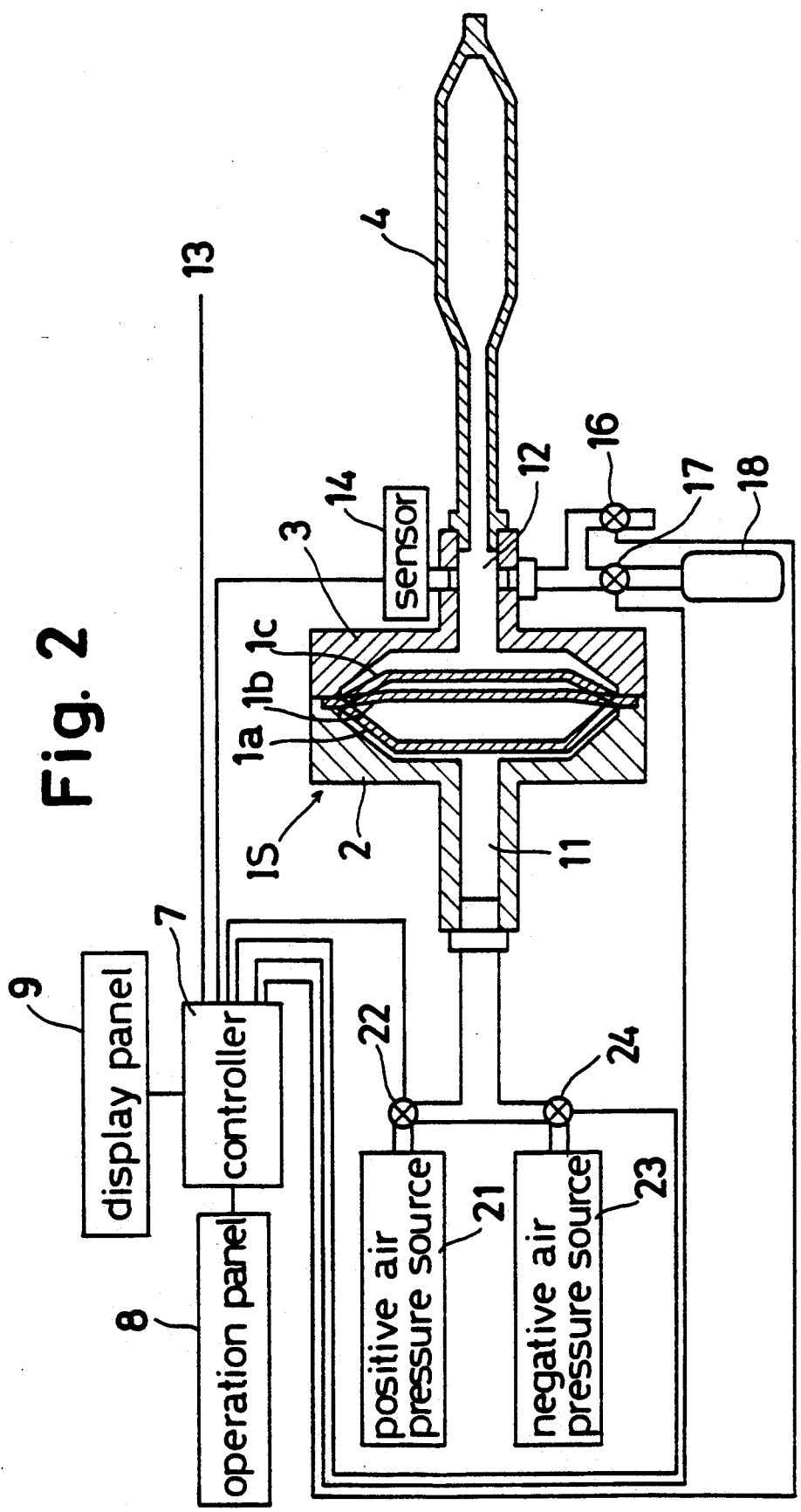
FIG. 2 is a view for showing an operation of an apparatus shown in FIG. 1.

An overall operation of the pumping device as mentioned above will be described hereinbelow. In FIG. 2, the membrane 1 is set to be moved between a position 1a and a position 1c which correspond to the fully expanded condition and the fully contracted condition of the balloon pump 4, respectively, when the amount of helium is normal. Under the normal mode of operation of the pumping device, if the first timing valve 22 is opened after closing the second timing valve 24, the balloon pump 4 begins to expand. After the elapse of the time t(int) which has been previously set-up or determined, the first timing valve 22 is closed, resulting in the completion of the expansion of the balloon pump 4 under which the pressure (10 mmHg in this embodiment) in the second chamber 12 is slightly greater than the maximum blood pressure of the aorta of the patient. At this time, the termination of the pressure increase in the second chamber 12 enables a rapid or quick establishment of the expansion of the balloon pump 4 and prevents an unexpected affection of the balloon pump 4 as a result of the unneccessary application of high pressure to the balloon pump 4 while its expanded condition is being held or maintained.

Decreasing the degree of the assistance degree of balloon pump 4 can be established by decreasing the time t in comparison with the time (int). This leads to the termination of the expansion of the balloon pump 4 before the balloon pump 4 brought into its full or extremely expansion, and the resulting condition is being held or maintain. Such a result is equivalent to one which is obtained by decreasing the capacity of the balloon pump 4.

It is to be noted that during the foregoing operation the time t which determines the duration of the opening of the first timing valve 22 may not be set to zero. The reason is that setting the time to zero or establishing the formula of t=0 means the inoperation of the balloon pump 4, which may bring the occurrence of thrombus. In light of this, the minimum value t (min) of the time t is set to be 8 (msec).

In light of the fact that the first timing valve 22 is under the control of the controller 7, the gradual decreasing of the time t or the duration of the opening of the first timing valve 22 can be established by the preparation of a program which enables such a decreasing of the time t. As a result, the dependency of the patient on the balloon pump 4 can be reduced gradually.

As to how to realize the reduction of the dependency of the patient on the balloon pump 4, one method is to make the reduction of the dependency of the patient on the balloon pump 4 the function of the item. For example, if it is desired that the gradual establishment of the independency of the patient on the balloon pump 4 occurs within 60 minutes, first of all, 60 minutes is entered through the operation panel 8 into the controller 7. Upon completion of this entry, the controller 7 operates to subtract [(t (ini) - 8 ) / 60 ] from the current time t during which the first timing valve 22 is being opened every one minute. Thus, after the passing of the time of 60 minutes, the current time t becomes 8 msec as the minimum value of the time t. Thus, the independency of the patient from the balloon pump 4 can be established which monitoring the passing of the time t on the display panel 9, which enables the interruption of this operation through the operation panel 8 when the patient becomes bad for example.

The other method is to establish the inverse proportion of the dependency on the balloon pump 4 to the work load of the living heart of the patient. Since the increase of the work load of the living heart of the patient means the recovery of the function thereof, this method utilizes the work load of the living heart of the patient which is in proportion to the area s indicated by ① in FIG. 3. It is assumed that the initial area s of the portion ① is set to be s (ini). The controller 7 is set to calculate the area s of the portion ① by the built-in program. The relationship between the area s of the portion ① and the time during which the first timing valve 22 is being opened are set to be established as follows;

$t = t \text{ (ini) when } s \leq s \text{ (ini)}$ $t = t \text{ (ini)} \times s \text{ (ini)}/s \text{ when } s > s \text{ (ini)}$ Thus, as the living heart of the patient recovers, the dependency on the balloon pump 4 is reduced. In detail, in the conventional device, the dependency on the balloon pump 4 is represented as each asterisked portion whose area is slashed (only one is indicated) in the middle graph in FIG. 3, from which no changes are found to be made. Contrary to this, as shown by the graph at the bottom in FIG. 3, in the sequence of * 1, * 2, * 3, and * 4, the dependency on the balloon pump 4 is reduced.

It should be apparent to one skilled in the art that the above-described embodiment is merely illustrative of but a few of the many possible specific embodiments of the present invention. Numerous and various other arrangements can be readily devised by those skilled in the art without departing from the spirit and scope of the invention as defined in the following claims.

What is claimed is:

1. An apparatus for driving an intra-aorta balloon pump comprising:
    an isolator having a housing in which a first chamber and a second chamber are defined by a membrane, said second chamber being in communication with an intra-aorta balloon pump;
    a positive pressure source which is in fluid communication with the first chamber via a first timing valve;
    a negative pressure source which is in fluid communication with the first chamber via a second timing valve;
    a space defined between the second chamber and the intra-aorta balloon pump and containing an amount of operating fluid;
    a tank for storing therein the operating fluid;
    an inlet valve interposed between the tank and the space;
    an exhaust valve interposed between the space and atmosphere;
    sensor means for measuring pressure in the space; and
    controller means for controlling the first timing valve and the second timing valve to be opened and closed alternately in order to establish an alternating supply of the positive and negative pressures to the first chamber so that a time-duration during which the first timing valve is opened is decreased gradually upon passage of time.

2. An apparatus for driving an intra-aorta balloon pump in accordance with claim 1, wherein said controller means includes a controller and wherein the time-duration is set in such a manner that the expansion of the balloon pump is reduced upon the passage of time.

3. An apparatus for driving an intra-aorta balloon pump in accordance with claim 1, wherein said controller means includes a controller and wherein the time-duration is set so as to be in reverse proportion to an ability of a living heart of a patient to work.

4. An apparatus for driving an intra-aorta balloon pump in accordance with claim 1, including a display for indicating the passage of time.

* * * * *

UNITED STATES PATENT AND TRADEMARK OFFICE
CERTIFICATE OF CORRECTION

| | | |
|---|---|---|
| PATENT NO. | : | 5,300,017 |
| DATED | : | April 5, 1994 |
| INVENTOR(S) | : | Takashi ISOYAMA et al |

It is certified that error appears in the above-identified patent and that said Letters Patent is hereby corrected as shown below:

Title page:
In Section [30], delete "3-155273" and insert -- 3-152273 --.

Signed and Sealed this

Second Day of August, 1994

Attest:

BRUCE LEHMAN

Attesting Officer

Commissioner of Patents and Trademarks